United States Patent [19]

Neal

[11] Patent Number: 4,570,628

[45] Date of Patent: Feb. 18, 1986

[54] SURGICAL DRAPE

[76] Inventor: Richard M. Neal, 4193 W. Redondo Beach Blvd., Lawndale, Calif. 90260

[21] Appl. No.: 579,860

[22] Filed: Feb. 13, 1984

[51] Int. Cl.⁴ ............................................ A61B 19/06
[52] U.S. Cl. ................................................ 128/132 D
[58] Field of Search ....................... 128/132 D, 132 R; 2/DIG. 7

[56] References Cited

U.S. PATENT DOCUMENTS

| | | | |
|---|---|---|---|
| 2,715,902 | 8/1955 | Shaffer et al. | 128/132 D |
| 3,452,750 | 7/1969 | Blawford | 128/132 D |
| 3,693,618 | 9/1972 | Madden | 128/132 D |
| 3,871,369 | 3/1975 | Krzewinski | 128/132 D |
| 4,105,019 | 8/1978 | Haswell | 128/132 D |
| 4,378,794 | 4/1983 | Collins | 128/132 D |
| 4,462,396 | 7/1984 | Wichman | 128/132 D |
| 4,471,769 | 9/1984 | Cockhart | 128/132 D |
| 4,476,860 | 10/1984 | Collins et al. | 128/132 D |

Primary Examiner—Gene Mancene
Assistant Examiner—John G. Weiss
Attorney, Agent, or Firm—Roger A. Marrs

[57] ABSTRACT

A surgical drape composed of a main sheet of sheet material adapted for use by a patient in the lithotomy position. The surgical drape is fabricated from a main sheet of sheet material which is constructed of sufficient softness and is sufficiently inexpensive to be disposable. The main sheet is formed of a torso section and a bottom section which are interconnected by a pair of side sections. Each side is formed into an enclosed area so as to function as a legging for the patient. The main sheet includes a fenestration centrally located therein with a fenestration strengthening material located entirely about said fenestration. The fenestration strengthening material is to resist tearing and cutting. A layer of non-liquid absorbing protective material is attached to the fenestration strengthening material. A collection container in the form of a flexible walled bag is located adjacent the bottom section. The collection material is adapted to collect blood and solids which are discharged during the medical procedure. A volumetric measuring indicia is carried in the exterior wall of the bag to facilitate the ascertaining of the approximate loss of blood by the patient. In another construction, a second container is provided for collection of fecal matter and a multiplicity of slots, pockets and holders are employed for yieldably retaining a variety of medical implements and supplies.

5 Claims, 6 Drawing Figures

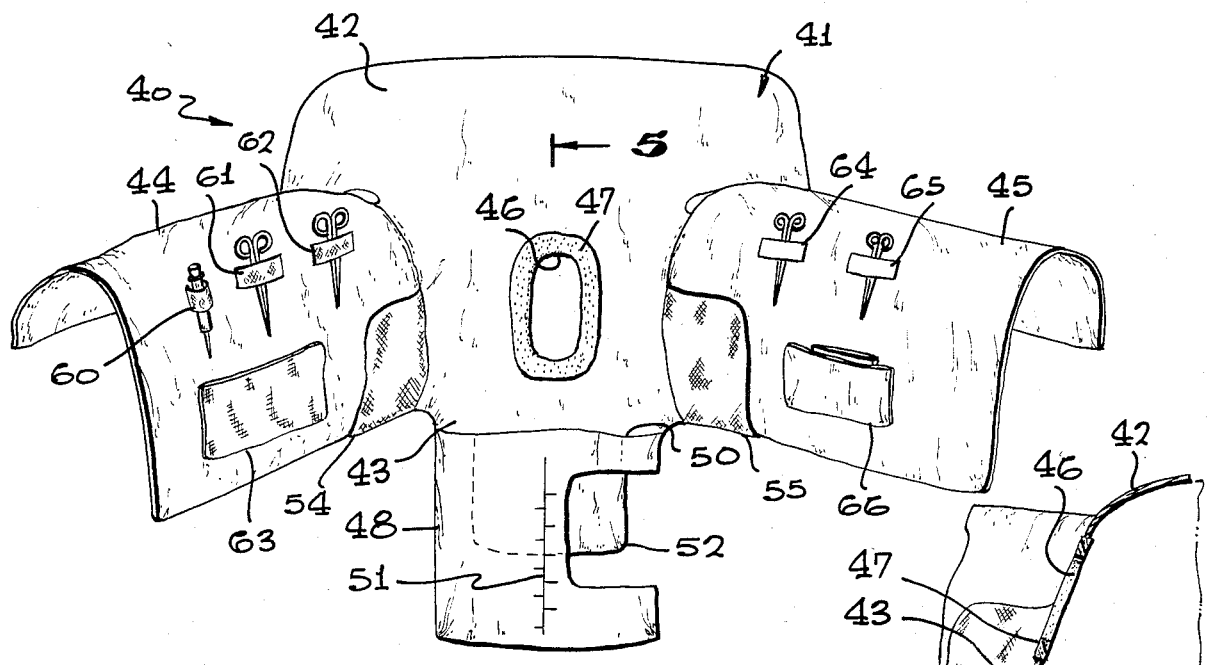
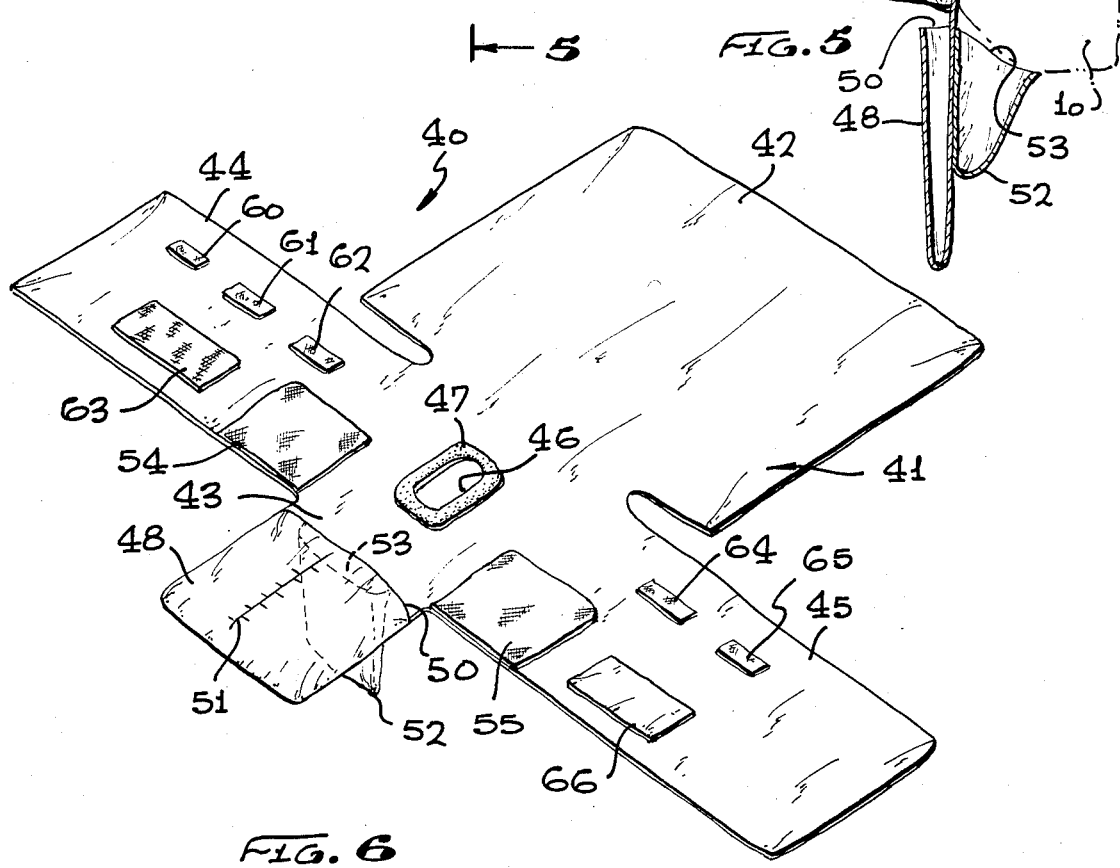

SURGICAL DRAPE

BACKGROUND OF THE INVENTION

1. Field of the Invention

The present invention relates generally to a surgical drape and, more particularly, to a surgical drape of an improved construction which has integral leggings therein and which is particularly adapted for use on a patient while in the lithotomy position and incorporating collection bags and medical implements and supply retainers.

2. Brief Description of the Prior Art

It has long been known to use some form of a surgical drape during the performing of a surgical procedure upon a woman in the area of the vagina. These common types of surgical operations are a cystoscopy procedure and a lithotomy procedure. Normally, these surgical drapes are composed of separate articles with a gap to be provided between the articles in the area of the vagina so as to facilitate the performing of the operation. The separate articles are cumbersome and do not facilitate application to the patient. There has been a definite need for a single pieced surgical drape which is to be used by a patient in the lithotomy position.

Additionally, during the performing of the operation, there will inherently be a blood loss and an emitting of solid particles. The normal procedure is for these solid particles and blood to be conducted into a waste collection are usually formed within the table upon which the operation is being performed. This material is then discharged. There has never been any way to arrive at an approximate amount of blood loss by the patient so that the blood can be reasonably and accurately replaced. There is a definite need for incorporating some type of liquid collecting container in conjunction with the surgical drape so as to make a reasonable estimate as to the amount of blood lost by the patient.

Additionally, surgical drapes of the prior art were constructed of a cloth material and were intended to be cleaned and reused. Reuse of such a drape inherently increases the possibility of the transfer of infection. If a surgical drape could be constructed to be sufficiently inexpensive to be disposable, such would be most desirable since the transfer of infection between patients by means of the surgical drape would be eliminated.

Furthermore, medical implements and supplies such as scissors, sutures, sponges, etc., are stored on a nearby table which is relatively remote from the surgical site which is inconvenient and cumbersome for the doctor. Therefore, a need exists to provide implement holders, medical supply retainers and waste collection pouches.

SUMMARY OF THE INVENTION

The structure of this invention is summarily described in the Abstract of the Disclosure and reference is to be had thereto.

The primary object of this invention is to construct a surgical drape which includes a liquid collection container, with this container including a volumetric measuring means so as to ascertain the amount of blood loss by the patient during the surgical procedure. Other collection pouches may be employed for gathering body waste materials.

Another object of this invention is to provide a surgical drape having integral leggings therein which can be easily applied to the patient in the lithotomy position with a minimum of effort.

Still another object of the present invention is to provide a novel vaginal drape having a plurality of holders and retainers for surgical implements and medical supplies that are readily accessible to the doctor during the performance of a medical procedure.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description, taken in connection with the accompanying drawings in which:

FIG. 4 is a front elevational view of another version of the surgical drape incorporating the present invention;

FIG. 5 is a fragmentary cross-sectional view taken in the direction of arrows 5—5 of FIG. 4; and FIG. 6 is a front layout view in perspective of the drape shown in FIG. 4.

DESCRIPTION OF THE PREFERRED EMBODIMENT

Figure 1:
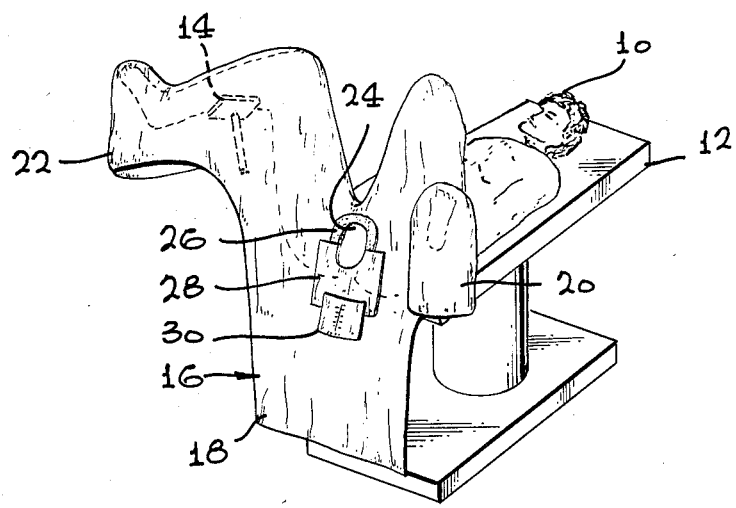
FIG. 1 is an isometric view of a patient in the lithotomy position with the surgical drape of the present invention placed on the patient.
Figure 2:
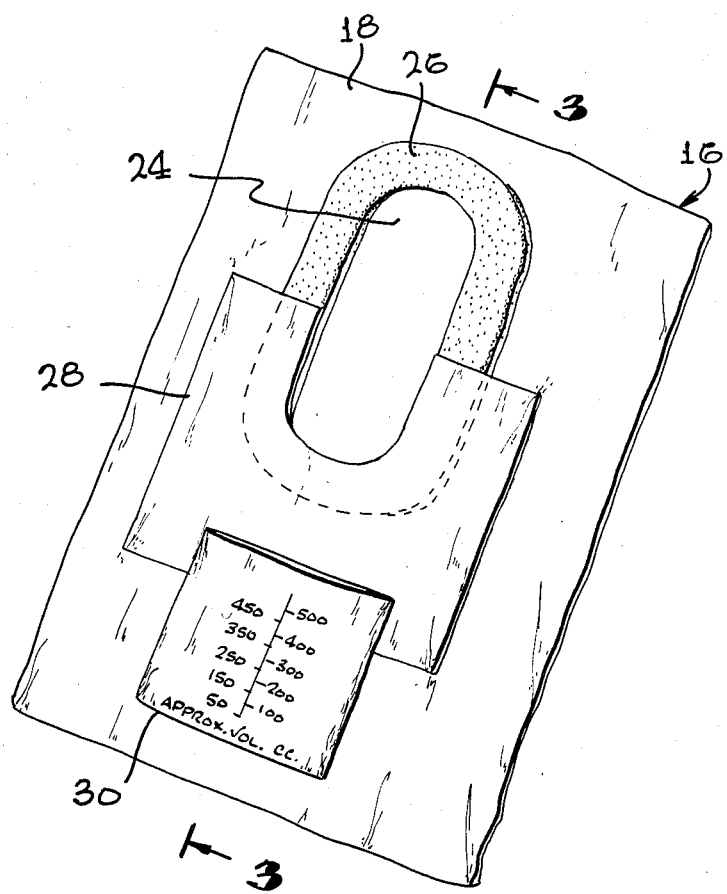
FIG. 2 is a fragmentary view of an enlarged center portion of the surgical drape of this invention.
Figure 3:
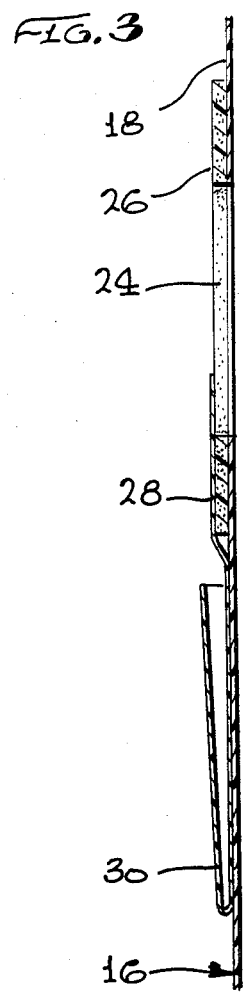
FIG. 3 is a cross-sectional view through the surgical drape of this invention taken along line 3—3 of FIG. 2.

Referring particularly to the drawing, there is shown a patient 10 mounted on a table 12, with the patient's legs being supported on a stirrup assembly 14 which is attached to the table 12. The surgical drape 16 of this invention is placed upon the patient 10 as shown in FIG. 1 of the drawing.

The surgical drape 16 takes the form of a main sheet 18 which has an upper or torso section and a lower bottom section which are interconnected by side sections. Each side section is formed into enclosed areas defining leggings 20 and 22. The main sheet 18 is constructed of a soft material such as a soft plastic or paper material so as to facilitate comfort to the patient 10. The material of construction of the main sheet 10 should be sufficiently inexpensive so as to facilitate disposability.

Centrally disposed within the main sheet 18 is located a fenestration 24. This fenestration 24 is of sufficient size and shap so as to provide access to the crotch area of the patient 10 in order to facilitate the performing of certain medical procedures. Surrounding the opening 24, there is a continuous fenestration stengthening material 26. This material 26 encircles the opening 24 and has an opening therein which is basically similar to and corresponds to opening 24. A typical material of construction of the material 26 would be a plastic foam material. The basic shape of the material 26 would be a ring-shape.

Attached to the exterior surface of the main sheet 18 and also attached to the bottom side of the material 26 is a protective sheet 28. This sheet 28 would normally be of a non-liquid absorbing material, such as plastic. The purpose of the sheet 28 is so that liquids and solids can flow thereover and be conductible into a collection chamber 30. The collection chamber 30 takes the form of a flexible walled bag. The bag 30 is attached to the protective sheet 28 and may also be attached to the main sheet 18. One edge of the open mouth of the bag 30 is to be entirely secured to the protective sheet 28 so as to cause the released liquid and solids to move over this edge and be conducted into the interior of the bag 30.

In order to facilitate ascertaining the amount of blood lost by the patient, on the exterior surface of the bag 30, there is located volumetric measuring indicia. By merely observing the level of accumulated liquid within the bag 30, an individual can readily determine the quantity of blood lost by the patient.

Referring now in detail to FIGS. 4-6 inclusive, another embodiment of the present invention is illustrated in the general direction of arrow 40 which takes the form of a main sheet 41 having an upper or torso section 42 and a lower or bottom section 43 which is interconnected by leg or side sections 44 and 45 respectively. Each leg or side section is formed into enclosed area defining leggings or wraps intended to enclose or drape over the legs of the patient. The main sheet 41 is constructed of a soft material such as a soft plastic or paper material and the material of construction is sufficiently inexpensive whereby the entire drape may be considered disposable or of a throw away nature.

Centrally disposed within the main sheet 41, there is an opening 46 of sufficient size and shape so as to accommodate access therethrough to the area of the patient being worked upon by the physician or doctor. Surrounding the opening 46, there is provided a continuous loop or circle of strengthening material 47. This material 47 encircles the opening 46 and is provided with a mating or corresponding opening therein. A typical material of construction of the material 47 is a foam plastic material and the basic shape of the material would be an oval or ring-shape or configuration.

Attached to the lower or bottom section 43 of the main sheet 41, a collection bag or pouch 48 is attached having an opening 50 adapted to receive and collect any released fluid or solids which may pass from the patient over the lower section 43 and into the bag or pouch 48. In order to facilitate ascertaining the amount of blood lost by the patient, a volumetric measuring indicia is carried on the external surface of the bag 48 and is indicated in general by the numeral 51.

Disposed immediately behind the bag 48, there is a pouch 52 having a reverse opening from the opening 50 on pouch 48 so as to be in position for receiving fecal matter from the patient during the performing of the medical procedure. As shown more clearly in FIG. 5, the bag 48 opens on one side of the lower section of the drape while the opening 53 of the pouch 52 faces the rear side of the drape lower portion 43 immediately adjacent the buttocks of the patient 10. Therefore, it can be seen that the bag 51 and pounch 52 downwardly depend from the lower or bottom section 43 and that the openings to the respective bag and pouch are on opposite sides of the drape lower portion 43.

Furthermore, it can be seen in FIGS. 4 and 6 that stretch material as indicated by numerals 54 and 55 couple portions of each leg section to the main sheet 41. This permits the material to stretch in order to conform to the body position of the patient 10 and results in better access by the doctor to the patient. Also, each leg section 44 and 45 is provided with a plurality of medical implement and supply holders so that a variety of implements and supplies can be immediately at the physicians's hand for use. As an example, the leg section 44 includes strips 60 for holding a syringe, a strip 61 for holding a scissors and a strip 62 for holding a suture needle. Also, a pocket 63 in carried for holding sterile gauze or other medical supplies. With respect to leg section 45, additional strips 64 and 65 are employed for appropriate medical implements useful in performing a medical precedure and an open pocket 66 is employed for receiving contaminated gauze, sutures or the like.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A surgical drape comprising:
a main sheet having a torso covering section and a bottom section interconnected by a pair of side sections, said main sheet being constructed of an inherently soft material and sufficiently inexpensive material to be disposable;
each said side section forming a substantially enclosed area so as to function as a legging;
said main sheet having a fenestration generally centrally located therein;
a fenestration strengthening material located entirely about said fenestration and attached to said main sheet, said fenestration strengthening material resisting tearing and cutting of the wall of said fenestration;
a layer of protective material attached to both said main sheet and said fenestration strengthening material, said layer of protective material to be nonliquid absorbing;
a collection container attached to said layer of protective material adjacent said bottom section, whereby said collection container is adapted to collect blood and solids which are discharged during the medical procedure;
said layer of protective material comprising a sheet of plastic;
said collection material comprising a flexible walled plastic bag;
said flexible walled plastic bag including means to ascertain volumetric measuring of the collected solids and liquids;
said means comprising measuring indicia located on said flexible walled bag;
a plurality of medical implement and supply holders arranged in fixed spaced apart relationship on each of said side section leggings for releasably retaining surgical implements and medical supplies; and
a second container having an open entrance carried immediately behind said first mentioned container and downwardly depending from said bottom section.

2. A surgical drape comprising:
a main sheet having a torso covering section and a bottom section interconnected by a pair of side sections, said main sheet being constructed of an inherently soft material and sufficiently inexpensive to be disposable;
each said side section forming a substantially enclosed area so as to function as a legging;
said main sheet having a fenestration generally centrally located therein;

a fenestration strengthening material located entirely about said fenestration and attached to said main sheet, said fenestration strengthening material resisting tearing and cutting of the wall of said fenestration;

a collection container attached to said bottom section, whereby said collection container is adapted to collect blood and solids which are discharged during the medical procedure; and a second collection container attached to said bottom immediately adjacent to and behind said first collection container.

3. The surgical drape as defined in claim 2 including:
said containers having openings at their attachments to said bottom section and each opening facing opposite to the other opening.

4. The surgical drape as defined in claim 3 including:
stretch material joining each of said side leggings to said bottom section.

5. The surgical drape as defined in claim 4 further including:
medical implement and supply storage holders and pockets carried on each of said side leggings for retaining implements, tools and disposable supplies.

* * * * *